US00RE49340E

(19) United States
(12) Reissued Patent
Tseng et al.

(10) Patent Number: US RE49,340 E
(45) Date of Reissued Patent: Dec. 20, 2022

(54) USE OF KNOWN COMPOUNDS AS D-AMINO ACID OXIDASE INHIBITORS

(71) Applicants: Yufeng Jane Tseng, Stafford, VA (US); National Taiwan University, Taipei (TW); National Yang Ming Chiao Tung University, Hsinchu (TW); National Health Research Institutes, Miaoli County (TW)

(72) Inventors: Yufeng Jane Tseng, Stafford, VA (US); Yu-Li Liu, Miaoli County (TW); Chung-Ming Sun, Hsinchu (TW); Hai-Gwo Hwu, Taipei (TW); Chih-Min Liu, Taipei (TW); Wen-Sung Lai, Taipei (TW)

(73) Assignees: Yufeng Jane Tseng, Stafford, VA (US); National Taiwan University, Taipei (TW); National Yang Ming Chiao Tung University, Hsinchu (TW); National Health Research Institutes, Miaoli County (TW)

(21) Appl. No.: 16/401,892

(22) Filed: May 2, 2019

Related U.S. Patent Documents

Reissue of:
(64) Patent No.: 9,868,975
Issued: Jan. 16, 2018
Appl. No.: 15/125,716
PCT Filed: Apr. 30, 2015
PCT No.: PCT/US2015/028385
§ 371 (c)(1),
(2) Date: Sep. 13, 2016
PCT Pub. No.: WO2015/168346
PCT Pub. Date: Nov. 5, 2015

U.S. Applications:
(60) Provisional application No. 61/986,480, filed on Apr. 30, 2014.

(51) Int. Cl.

| | |
|---|---|
| ***C12Q 1/26*** | (2006.01) |
| ***G16C 20/60*** | (2019.01) |
| ***G16C 20/64*** | (2019.01) |
| ***G16B 35/00*** | (2019.01) |
| ***A61K 31/341*** | (2006.01) |
| ***A61K 31/4439*** | (2006.01) |
| ***A61K 31/451*** | (2006.01) |
| ***A61K 31/4706*** | (2006.01) |
| ***A61K 31/485*** | (2006.01) |
| ***A61K 31/551*** | (2006.01) |
| ***G01N 33/00*** | (2006.01) |

(52) U.S. Cl.
CPC ..... *C12Q 1/26* (2013.01); *A61K 31/341* (2013.01); *A61K 31/4439* (2013.01); *A61K 31/451* (2013.01); *A61K 31/4706* (2013.01); *A61K 31/485* (2013.01); *A61K 31/551* (2013.01); *G01N 33/00* (2013.01); *G16B 35/00* (2019.02); *G16C 20/60* (2019.02); *G16C 20/64* (2019.02); *G01N 2333/90644* (2013.01); *G01N 2500/04* (2013.01); *G01N 2800/2814* (2013.01); *G01N 2800/302* (2013.01)

(58) Field of Classification Search
CPC ..... C12Q 1/26; A61K 31/341
See application file for complete search history.

(56) References Cited

U.S. PATENT DOCUMENTS

2009/0264653 A1 10/2009 Bartolini et al.

OTHER PUBLICATIONS

Bromundt et al.: "Sleep-wake Cycles and Cognitive Functioning in Schizophrenia," British Journal of Psychiatry; Apr. 1, 2011, vol. 198, No. 04, pp. 269-276.

Haenisch et al.: "Risk of Dementia in Elderly Patients with the Use of Proton Pump Inhibitors," European Archives of Psychiatry and Clinical Neuroscience; Oct. 24, 2014, vol. 265, No. 5, pp. 419-428.

Khazaal et al.: "Eating and weight related cognitions in people with Schizophrenia: A case control study". Clinical Practice and Epidemiology in Mental Health; Oct. 31, 2006, vol. 2, No. 1.

Yang et al.: "The DAO Gene is Associated with Schizophrenia and Interacts with Other Genes in the Taiwan Han Chinese Population," PLOS ONE; Mar. 28, 2013, vol. 8, Issue. 3, p. e60099.

Burnet et al. "D-Amino Acid Oxidase Activity and Expression are Increased in Schizophrenia" Molecular Psychiatry vol. 13, pp. 658-660, 2008.

Heresco-Levy et al. "D-Serine Efficacy as Add-On Pharmacotherapy to Risperidone and Olanzapine for Treatment-Refractory Schizophrenia" Biological Psychiatry vol. 57, pp. 577-585, 2005.

(Continued)

*Primary Examiner* — Padmashri Ponnaluri
(74) *Attorney, Agent, or Firm* — Cesari & McKenna, LLP

(57) ABSTRACT

The invention utilizes virtual screening strategy to seek for current market drugs as anti-schizophrenia therapy drug repurposing. Drug repurposing strategy finds new uses other than the original medical indications of existing drugs. Finding new indications for such drugs will benefit patients who are in needs for a potential new therapy sooner since known drugs are usually with acceptable safety and pharmacokinetic profiles. In this study, repurposing marketed drugs for DAAO inhibitor as new schizophrenia therapy was performed with virtual screening on marketed drugs and its metabolites. The identified and available drugs and compounds were further confirmed with in vitro DAAO enzymatic inhibitory assay.

13 Claims, 8 Drawing Sheets

(56) References Cited

OTHER PUBLICATIONS

Katane et al. "Identification of Novel D-Amino Acid Oxidase Inhibitors by In Silico Screening and Their Functional Characterization In Vitro" Journal of Medicinal Chemistry, 2012.
Li et al. "Pharmacokinetic Drug Interaction Profile of Omeprazole with Adverse Consequences and Clinical Risk Management" Therapeutics and Clinical Risk Management vol. 9, pp. 259-271, 2013.
Maderia et al. "Increased Brain D-Amino Acid Oxidase (DAAO) Activity in Schizophrenia" Schizophrenia Research vol. 101, pp. 76-83, 2008.
Novick et al. "SWEETLEAD: An In Silico Database of Approved Drugs, Regulated Chemicals, and Herbal Isolates for Computer-Aided Drug Discovery" PLOS ONE vol. 8, pp. 1-9, 2013.
Sacchi et al. "Structure-Function Relationships in Human D-Amino Acid Oxidase" Amino Acids vol. 43, pp. 1833-1850, 2012.
Sparey et al. "The Discovery of Fused Pyrrole Carboxylic Acids as Novel, Potent D-Amino Acid Oxidase (DAO) Inhibitors" Bioorganic and Medicinal Chemistry Letters vol. 18, pp. 3386-3391, 2008.
Tsai et al. "D-Serine Added to Clozapine for the Treatment of Schizophrenia" American Journal of Psychiatry vol. 156, pp. 1822-1825, 1999.
Lewis, R., Hawley's Condensed Chemical Dictionary, 15th ed., 2007, excerpt p. 711.*
Risbood, V. et al., . Pharm Prac. 2010 vol. 23, Poster Submission at p. 167.*
Wagner, S. et al., Eur. J. Clin. Pharmacol. 2011 vol. 67, pp. 533-534.*
Abelo, A. et al., Drug Metab. Dispos. 2000 vol. 28, pp. 966-972.*
Silva, T. et al., Mini-Rev. Med. Chem. 2005 vol. 5 pp. 893-914.*

* cited by examiner

USE OF KNOWN COMPOUNDS AS D-AMINO ACID OXIDASE INHIBITORS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

This application is the National Stage of International Application No. PCT/US2015/028385, filed on Apr. 30, 2015, which claims the benefit of U.S. Provisional Application No. 61/986,480, filed on Apr. 30, 2014. The contents of both applications are hereby incorporated by reference in their entirety.

FIELD OF THE INVENTION

The invention relates to D-amino acid oxidase (DAAO) inhibitors. Particularly, the invention relates to selection of known compounds as DAAO inhibitors.

BACKGROUND OF THE INVENTION

The aberrant regulatory mechanism of glutamate transmission on N-methyl-D-aspartic acid (NMDA) receptor has been reported as one of the neuropathology in schizophrenia. The receptor is a heterotetramer composed of two structure subunits of NMDA receptor 1 (NR1) and NR2. The extracellular domain of these two subunits were responsible for modulatory and ligand binding functions, where the NR1 binds the co-agonist glycine, and the NR2 binds the neurotransmitter glutamate. The membrane channel domain is responsible for the entrance of calcium ions. The receptor requires the binding of glutamate from NR2 subunit to activate the receptor, and requires the co-agonist of glycine binding for the efficient opening of the ion channel. Modulation the glycine binding site of NMDA receptor may improve the cognitive function and negative symptoms in schizophrenia. D-amino acid oxidase (DAAO) was found to be involved in the activation process of the NMDA receptor. The substrates of DAAO, especially the D-serine, may bind to the glycine site of the NMDA receptor as a co-agonist. This in turn may regulate the NMDA receptor in opening its calcium channel. D-serine has been found to inhibit the α-amino-3-hydroxy-5-methyl-4-isoxazole propionic acid (AMPA) receptor-mediated current in rat hippocampus neurons (Gong, X. Q. et al., Canadian Journal of Physiology and Pharmacology 2007, 85 (5), 546-55). Thus, DAAO was hypothesized to be implicated in the pathogenesis of schizophrenia. As the NMDA receptor also involved in affective disorder (Kaster, M. P. et al., Pharmacological reports: PR 2012, 64 (3), 706-13), it is likely that inhibiting the DAAO may elevate the function of NMDA and improve both the symptoms of schizophrenia and depression affective disorder (Hashimoto, K. et al.. European Archives of Psychiatry and Clinical Neuroscience 2013).

Schizophrenia is a devastating mental disorder that afflicts approximately 1 percent of the worldwide population. The direct and indirect costs associated with this disorder make it extremely expensive (Abbott A. Nature, 2010; 468: 158-9). Clinically, schizophrenia is mainly characterized by positive symptoms, including delusions and hallucinations, negative symptoms, such as blunted emotions, anhedonia, and social isolation, and cognitive deficits such as the impairment of executive function, attention, and working memory. The initial and most common hypothesis regarding pathophysiology of schizophrenia originated from the antipsychotic treatments is dopamine hypothesis, especially for the treatment of positive symptoms (Howes, O. D; Kapur, S. Bulletin, 2009, 35(3), 549-62; Madras, B. K, Journal of the History of the Neurosciences, 2013, 22(1), 62-78). In contrast to positive symptoms, negative symptoms and cognitive deficits have not garnered considerable attention until recently. Unfortunately, the available antipsychotic medications are relatively ineffective at improving negative symptoms and cognitive deficits as well. After the initial discovery of antipsychotics for more than a half century, the field finds itself in need not only of alternative medications but also alternative targets, especially for negative and cognitive symptoms (Abbott A. Nature, 2010; 468: 158-9).

As a starting point from a neurotransmitter-based theory, hypofunction of N-methyl-D-aspartate receptor (NMDAR)-mediated signaling pathways has been cumulatively implicated in the associated learning, social impairments, long-term potentiation, and various types of learning and memory (Riedel G, Platt B, Micheau Behavioural Brain Res. 2003; 140:1-47). The involvement of the NMDAR system in schizophrenia is evidenced by the observations that NMDAR antagonists (i.e., phencyclidine (PCP) and ketamine) induced negative symptoms and cognitive dysfunction similar to that of schizophrenia, suggesting NMDAR may be particular relevant to persistent, poor-outcome forms of schizophrenia (Moghaddam B, Javitt D. Neuropsychopharmacology, 2012; 37: 4-15). Although the effect of glutamatergic dysfunction on the etiology of schizophrenia remains unclear, accumulating studies also suggest that dysregulation of glutamatergic neurotransmission may be involved in the pathophysiology of schizophrenia (Goff D C, Coyle J T. Am J Psychiatry, 2001; 158: 1367-77; Moghaddam B. Neuron, 2003; 40: 881-4; Lin C H, Lane H Y, Tsai G E. Pharmacol Biochem Behav, 2012; 100: 665-77). In the simplest version of the NMDAR models, the primary goal of treatment would be the restoration of function at the NMDAR itself or other targets beyond the NMDAR (Moghaddam B, Javitt D. Neuropsychopharmacology, 2012; 37: 4-15). Thus, the hypo-function of glutamatergic transmission in schizophrenic patients is a potential target of treatment and the drugs that enhance NMDARs function have been thought as the potential therapy (Lin C H, Lane H Y, Tsai G E. Pharmacol Biochem Behav, 2012; 100: 665-77). NMDARs are heteromeric complexes that contain NR1, NR2, and NR3 subunits. NMDARs also contain a glutamate recognition site in the NR2 subunit and a glycine modulatory site in the NR1 subunit. Both glutamate and glycine are agonists of the NMDARs (Clements J D, Westbrook G L. Activation kinetics reveal the number of glutamate and glycine binding sites on the N-methyl-d-aspartate receptor. Neuron, 1991; 7: 605-613). Since direct stimulation of the glutamate-binding site of NMDARs can produce excitotoxic neuronal death, the enhancement of NMDAR function by targeting glycine site or D-serine site of NMDAR may be more beneficial. One promising target is D-amino acid oxidase (DAO, DAAO) which is a flavoenzyme that metabolises D-serine, a co-agonist of the endogenous NMDAR. As such, it has the potential to modulate NMDAR function and to contribute to the widely hypothesized involvement of NMDAR signalling in schizophrenia. On the same vein, accumulating data from three lines of evidence support for this possibility (L Verrall, P W J Burnet, J F Betts, and P J Harrison, Mol Psychiatry 2010 February; 15(2): 122-137). (1) DAO shows genetic associations to the disorder in several but not all studies; (2) the expression and activity of DAO are increased in schizophrenia; and (3) the inactivation of DAO resulted in behavioral and biochemical effects in rodents, suggesting potential therapeutic benefits. Because NMDAR dysfunction is considered to be involved in the positive, negative and cognitive symptoms of schizophrenia, there has been much interest in developing potent and selective DAO inhibitors for the treatment of negative and cognitive symptoms of schizophrenia (Sean M Smith, Jason M Uslaner, and Peter H Hutson, Open Med Chem J. 2010; 4: 3-9).

It has been reported that NMDA receptor enhancer has the following indications: (i) treatment for all symptom domains of schizophrenia and schizoaffective disorder, including negative, cognitive, depressive, positive and general psychopathology symptom domains (Tsai, G. E. and P. Y. Lin, Curr Pharm Des, 2010. 16(5): p. 522-37; and Singh, S. P. and V. Singh, CNS Drugs, 2011. 25(10): p. 859-85); (ii) treatment for depression (Huang, C. C., et al., Biol Psychiatry, 2013. 74(10): p. 734-41); (iii) treatment for Parkinson's disease (Gelfin, E., et al., Int J Neuropsychopharmacol, 2012. 15(4): p. 543-9; (iv) treatment for Tourette Syndrome (Singer, H. S., C. Morris, and M. Grados, Med Hypotheses, 2010. 74(5): p. 862-7); (v) treatment for mild cognitive impairment (MCI) and Alzheimer disease (AD) (Lin, C. H., et al., Biol Psychiatry. 2014. 75(9): p. 678-85); (vi) treatment for Post-traumatic stress disorder (PTSD) (Heresco-Levy, U., et al., Int J Neuropsychophannacol, 2009. 12(9): p. 1275-82; Difede, J., et al., Neuropsychopharmacology, 2014. 39(5): p. 1052-8); (vii) treatment for Obsessive-compulsive disorder (OCD) (Wu. P. L., et al., J Clin Psychopharmacol, 2011. 31(3): p. 369-74; and Wilhelm, S., et al., Am J Psychiatry. 2008. 165(3): p. 335-41; quiz 409); (viii) analgesics (Gong, N., et al., Neuropharmacology, 2012. 63(3): p. 460-8).

D-serine is a full agonist at the allosteric glycine binding site of the NMDA receptor, and was reported to improve negative, cognitive symptoms, and symptoms poorly addressed by the standard D2 antagonist in schizophrenia (Ferraris, D. V. et al., Current pharmaceutical design 2011, 17 (2), 103-11) and in depression (Hashimoto, K et al., European Archives of Psychiatry and Clinical Neuroscience 2013). Inhibition of DAAO can increase the brain D-serine level directly therefore can be potentially used for the schizophrenia therapy (Miyamoto, S. et al., Molecular psychiatry 2012, 17 (12), 1206-27; Sacchi, S. et al., Current pharmaceutical design 2012; Ono, K. et al., Journal of neural transmission (Vienna, Austria: 1996) 2009, 116 (10), 1335-47) and even further for affective disorder.

Known inhibitors of DAAO include benzoic acid, pyrrole-2-carboxylic acids, and indole-2-carboxylic acids. Indole derivatives and particularly certain indole-2-carboxylates have been described in the literature for treatment of neurodegenerative disease and neurotoxic injury. EP 396124 discloses indole-2-carboxylates and derivatives for treatment or management of neurotoxic injury resulting from a CNS disorder or traumatic event or in treatment or management of a neurodegenerative disease. U.S. Pat. Nos. 5,373,018; 5,374,649; 5,686,461; 5,962,496 and 6,100,289 disclose treatment of neurotoxic injury and neurodegenerative disease using indole derivatives. WO 03/039540 disclose DAAO inhibitors, including indole-2-carboxylic acids, and methods of enhancing learning, memory and cognition as well as methods for treating neurodegenerative disorders. Patent Application No. WO/2005/089753 discloses benzisoxazole analogs and methods of treating mental disorders, such as Schizophrenia. Recently, compounds such as the AS057278 (5-methylpyrazole-3-carboxylic acid) (Adage, T. et al., Eur Neuropsychopharmacol 2008, 18 (3), 200-14), CBIO (6-chlorobenzo[d]isoxazol-3-ol) (Ferraris, D. et al., J Med Chem 2008, 51 (12), 3357-9) and 4H-thieno [3,2-b] pyrrole-5-carboxylic acid from Merck (Smith, S. M. et al., J Pharmacol Exp Ther 2009, 328 (3), 921-30) have been reported to have DAAO inhibitory effect.

There is a need to develop candidate drugs having DAAO inhibitory effect to treat various neurological and physical disorder.

DETAILED DESCRIPTION OF THE INVENTION

Figure 1A:
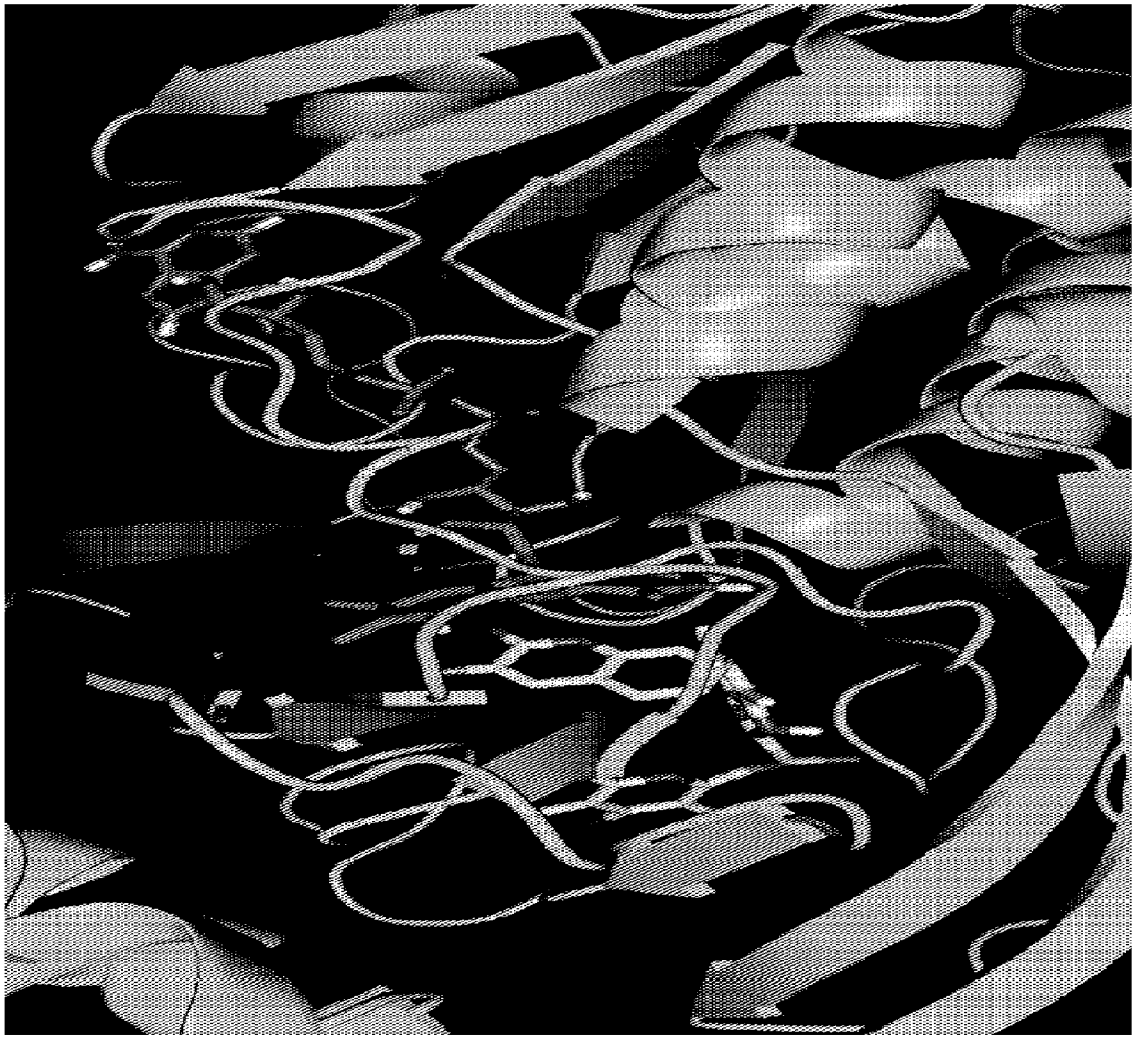
FIGS. 1a-1d show structural analysis for 5-0-Desmethyl-Omeprazole. (a) The comparison with 3-hydroxyquinolin-2 (1H)-one binding mode. (b) 5-0 Desmethyl-Omeprazole bound with DAAO-FAD complex (c) 2D structure of 5-0-Desmethyl-Omeprazole (d) Residues for 5-0-Desmethyl-Omeprazole binding. The green cartons showed DAAO structure. The pink, blue and yellow sticks displayed FAD, 3-hydroxyquinolin-2(1H)-one and 5-0-Desmethyl-Omepratole, respectively. The purple lines were the residues which interacted with 5-0-Desmethyl-Omeprazole. The yellow dashed lines were hydrogen bonding interactions.
Figure 1B:
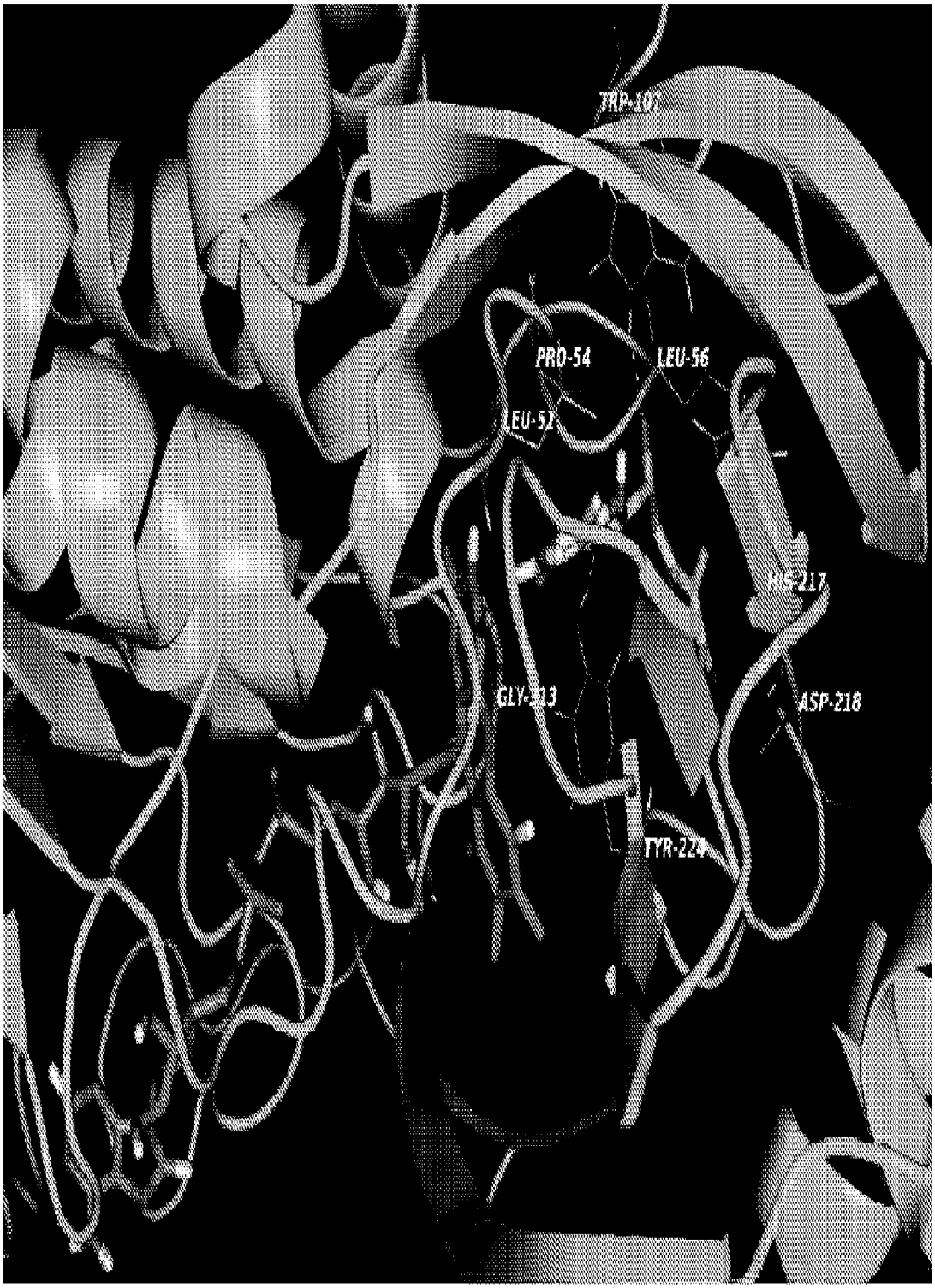
Figure 1C:
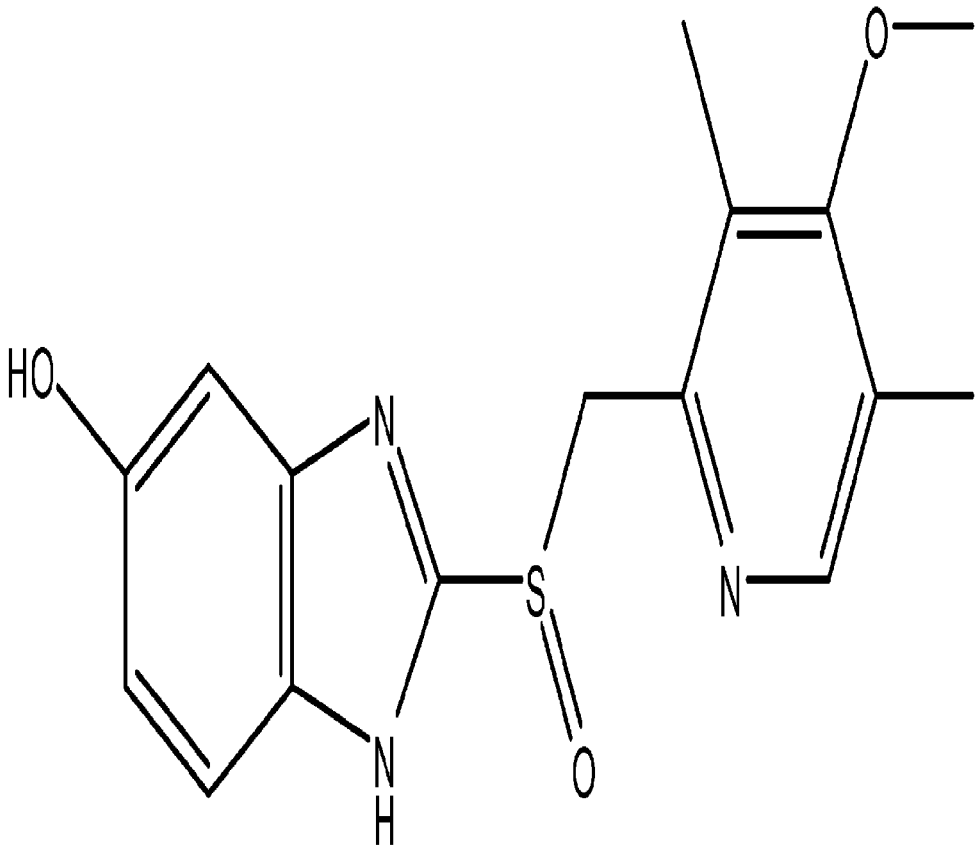
Figure 1D:
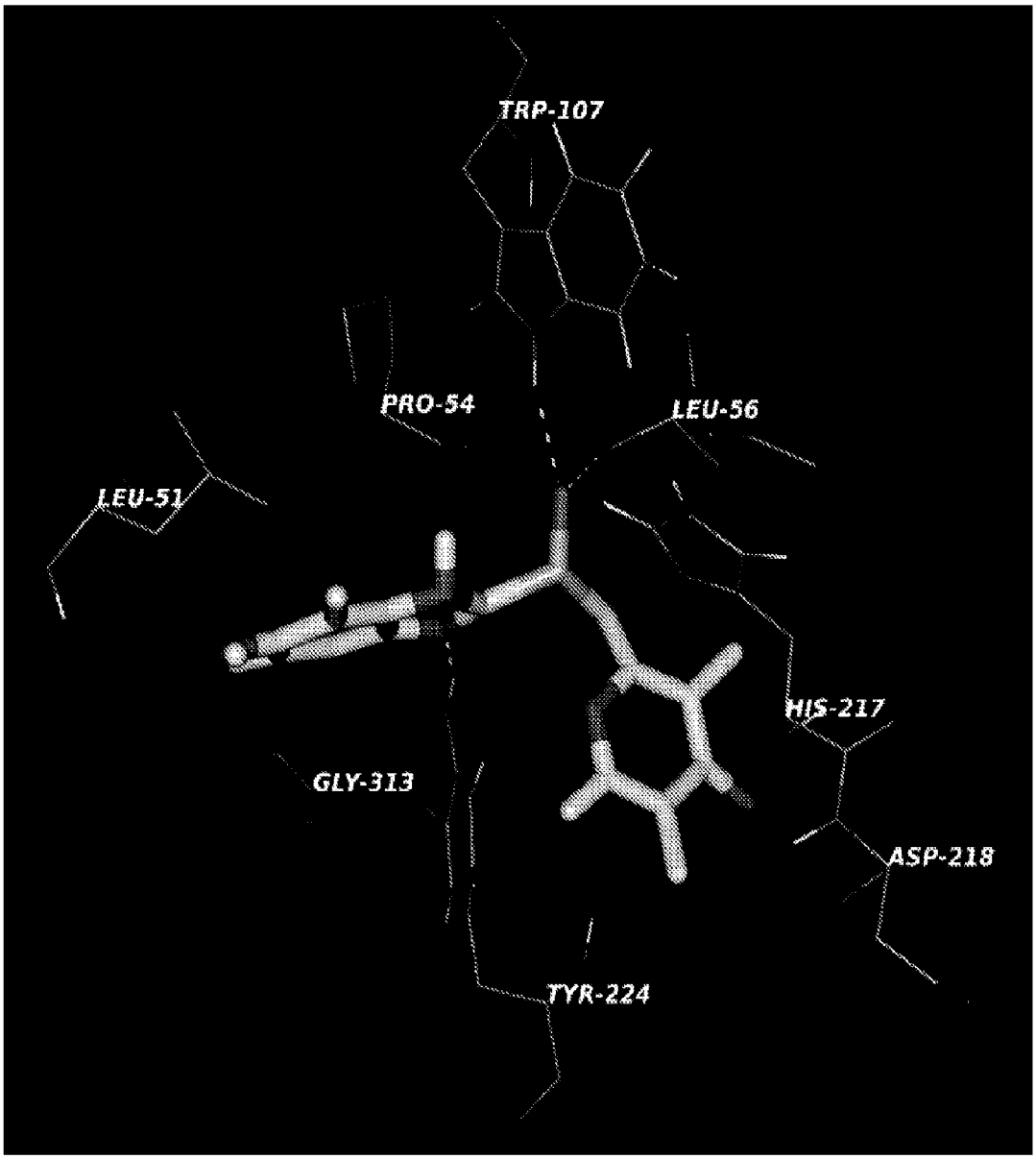

The invention is based on the idea of discovering the known drugs and compounds as potential DAAO inhibitors—drug repurposing, the structure-based virtual screening was performed with the drugbank database. The invention utilizes virtual screening strategy to seek for current market drugs as anti-schizophrenia therapy—drug repurposing. Drug repurposing strategy finds new uses other than the original medical indications of existing drugs. Finding new indications for such drugs will benefit patients who are in needs for a potential new therapy sooner since known drugs are usually with acceptable safety and pharmacokinetic profiles. In our work, repurposing strategy was applied for discovering DAAO inhibitor as new schizophrenia therapy was performed with virtual screening on marketed drugs and its metabolites. The identified and available drugs and compounds were further confirmed with in vitro DAAO enzymatic inhibitory assay.

All scientific and technical terms used in this application have meanings commonly used in the art unless otherwise specified. As used in this application, the following words or phrases have the meanings specified.

The terms "a" and "an" refer to one or to more than one (i.e., to at least one) of the grammatical object of the article.

The term "or" refers to "and/or" unless explicitly indicated to refer to alternatives only or unless the alternatives are mutually exclusive.

The term "subject" includes living organisms such as humans, monkeys, cows, sheep, horses, pigs, cattle, goats, dogs, cats, mice, rats, cultured cells, and transgenic species thereof. In a preferred embodiment, the subject is a human.

The term "administering" includes routes of administration which allow the active ingredient of the invention to perform their intended function.

The term "treat" or "treatment" refers to a method of reducing the effects of a disease or condition. Treatment can also refer to a method of reducing the underlying cause of the disease or condition itself rather than just the symptoms. The treatment can be any reduction from native levels and can be, but is not limited to, the complete ablation of the disease, condition, or the symptoms of the disease or condition.

The term "prevent," "prevention" or "preventing" means inhibition or averting of symptoms associated with the target disease.

The phrase "therapeutically effective amount" refers to that amount of a compound, material, or composition comprising a compound of the present invention which is effective for producing a desired therapeutic effect, at a reasonable benefit/risk ratio applicable to any medical treatment.

The term "neurological disorder" refers to any undesirable condition of the central or peripheral nervous system of a mammal. The term "neurological disorder" includes neurodegenerative diseases (e.g., Alzheimer's disease, Parkinson's disease and amyotrophic lateral sclerosis). neuropsychiatric diseases (e.g. schizophrenia and anxieties, such as general anxiety disorder). Exemplary neurological disorders include MLS (cerebellar ataxia), Huntington's disease, Down syndrome, multi-infarct dementia, status epilecticus, contusive injuries (e.g. spinal cord injury and head injury), viral infection induced neurodegeneration, (e.g. AIDS, encephalopathies), epilepsy, benign forgetfulness, closed head injury, sleep disorders, depression (e.g., bipolar disorder), dementias, movement disorders, psychoses, alcoholism, post-traumatic stress disorder and the like. "Neurological disorder" also includes any undesirable condition associated with the disorder. For instance, a method of treating a neurodegenerative disorder includes methods of treating loss of memory and/or loss of cognition associated with a neurodegenerative disorder. Such method would also include treating or preventing loss of neuronal function characteristic of neurodegenerative disorder.

In one aspect, the invention provides a method of treating and/or preventing a disease associated with DAAO inhibition in a subject, comprising administering to the subject an effective amount of a compound selected from the group consisting of: esomeprazole, olanzapine. 5-O-desmethyl-omprazole, (−)-trans 4-(4-Fluorophenyl)-3-(3-hydroxy-4-methoxyphenoxymethyl) piperidine (BRL 36583A), (−)trans 4-(4-fluorophenyl)-3-(4-hydroxy-3-methoxyphenoxymethyl)piperidine-hydrochloride (BRL 36610A), amodiaquin, duloxetine, nalbuphine and N-desmethylclozapine, or a therapeutically acceptable salt, solvate, prodrug or isomer thereof.

In another aspect, the invention provides a method of inhibiting aberrant regulatory mechanism of glutamate transmission on N-methyl-D-aspartic acid (NMDA) receptor in a subject, comprising administering to the subject an effective amount of a compound selected from the group consisting of: esomeprazole, olanzapine. 5-O-desmethyl-omprazole, (−)-trans 4-(4-Fluorophenyl)-3-(3-hydroxy-4-methoxyphenoxymethyl) piperidine (BRL 36583A), (−)trans 4-(4-fluorophenyl)-3-(4-hydroxy-3-methoxyphenoxymethyl) piperidine-hydrochloride (BRL 36610A), amodiaquin, duloxetine, nalbuphine and N-desmethylclozapine, or a therapeutically acceptable salt, solvate, prodrug or isomer thereof. Accordingly, the invention provides a use of a compound selected from the group consisting of: esomeprazole, olanzapine, 5-O-desmethyl-omprazole, (−)-trans 4-(4-Fluorophenyl)-3-(3-hydroxy-4-methoxyphenoxymethyl) piperidine (BRL 36583A), (−)trans 4-(4-fluorophenyl)-3-(4-hydroxy-3-methoxyphenoxymethyl) piperidine-hydrochloride (BRL 36610A), amodiaquin, duloxetine, nalbuphine and N-desmethylclozapine, or a therapeutically acceptable salt, solvate, prodrug or isomer thereof, in the manufacture of a medicament for inhibiting aberrant regulatory mechanism of glutamate transmission on N-methyl-D-aspartic acid (NMDA) receptor in a subject.

In another aspect, the invention provides a method of inhibiting hypo function of N-methyl-D-aspartate receptor (NMDAR)-mediated signaling pathway, in a subject, comprising administering to the subject an effective amount of a compound selected from the group consisting of: esomeprazole, olanzapine, 5-O-desmethyl-omprazole, (−)-trans 4-(4-Fluorophenyl)-3-(3-hydroxy-4-methoxyphenoxymethyl) piperidine (BRL 36583A), (−)trans 4-(4-fluorophenyl)-3-(4-hydroxy-3-methoxyphenoxymethyl) piperidine-hydrochloride (BRL 36610A), amodiaquin, duloxetine. nalbuphine and N-desmethylclozapine, or a therapeutically acceptable salt, solvate, prodrug or isomer thereof. Accordingly, the invention provides a use of a compound selected from the group consisting of: esomeprazole, olanzapine, 5-O-desmethyl-omprazole, (−)-trans 4-(4-Fluorophenyl)-3-(3-hydroxy-4-methoxyphenoxymethyl) piperidine (BRL 36583A), (−)trans 4-(4-fluorophenyl)-3-(4-hydroxy-3-methoxyphenoxymethyl) piperidine-hydrochloride (BRL 36610A), amodiaquin, duloxetine, nalbuphine and N-desmethylclozapine, or a therapeutically acceptable salt, solvate, prodrug or isomer thereof, in the manufacture of a medicament for inhibiting hypofunction of N-methyl-D-aspartate receptor (NMDAR)-mediated signaling pathway in a subject.

The structures of the above-mentioned compounds are listed below:

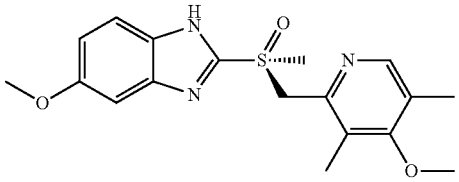

Esomerprazole

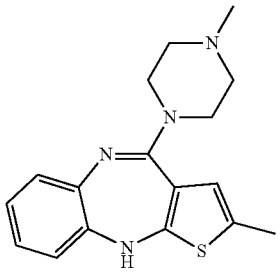

Olanzapine

-continued

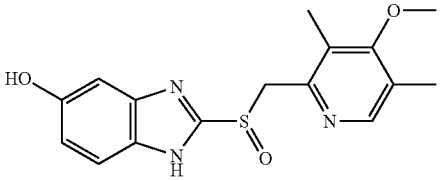

5-O-desmethyl-omeprazole

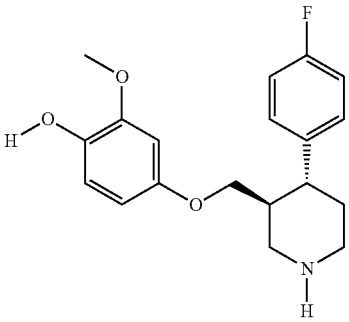

BRL 36610A

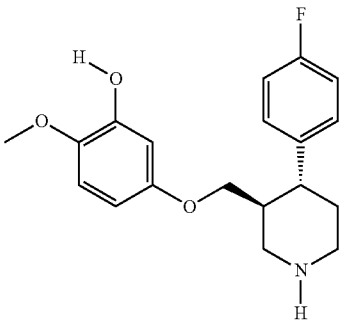

BRL 36583A

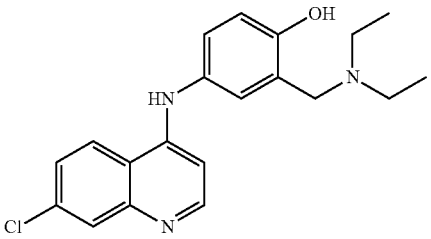

Amodiaquine

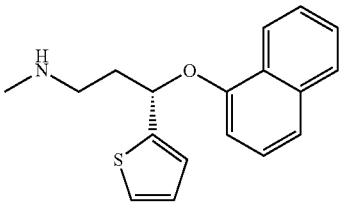

Duloxetine

-continued

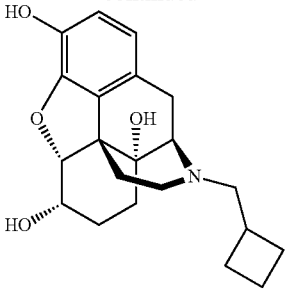

Nalbuphine

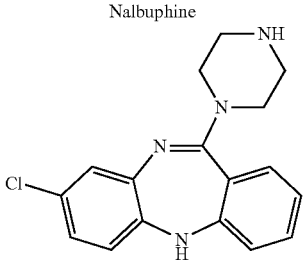

N-Desmethylclozapine

The compounds of the invention are useful for treating or preventing any disease and/or condition, wherein modulation of D-serine levels, and/or its oxidative products, is effective in ameliorating symptoms. Inhibition of the enzyme can lead to increases in D-serine levels and a reduction in the formation of toxic D-serine oxidation products. Thus, the invention provides methods for the treatment or prevention of neurological disorders and methods of enhancing learning, memory and/or cognition. The invenion also provides methods for the treatment or prevention of the disease mediated by DAAO inhibition; preferably, symptom domains of schizophrenia and schizoaffective disorder, depression, Tourette Syndrome, Post-traumatic stress disorder (PTSD), Obsessive-compulsive disorder (OCD), analgesics, loss of memory and/or cognition associated with neurodegenerative diseases or loss of neuronal function characteristic of neurodegenerative diseases. In some embodiments, the symptom domains of schizophrenia and schizoaffective disorder include negative, cognitive, depressive, positive and general psychopathology symptom domains. In another embodiment, the disease associated with DAAO inhibition is mild cognitive impairment (MCI), Alzheimer's disease, Parkinson's disease or schizophrenia. In some embodiments, the disease associated with DAAO inhibition is pain, ataxia or convulsion. In some embodiments, the compounds of the invention can be used for treating or preventing loss of memory and/or cognition associated with neurodegenerative diseases (e.g., Alzheimer's disease and schizophrenia) and for preventing loss of neuronal function characteristic of neurodegenerative diseases. Further, methods are provided for the treatment or prevention of pain, ataxia and convulsion.

In some embodiment, the effective amount of the compound described herein ranges from 2 mg/kg body weight to 5 g/kg body weight; preferably, 10 mg/kg body weight to 3 g/kg body weight or 20 mg/kg body weight to 2 g/kg body weight.

A pharmaceutically acceptable carrier, diluent, excipient, and/or salt means that the carrier, diluent, excipient and/or salt must be compatible with the active ingredient, does not adversely affect the therapeutic benefit of the active ingredient, and is not deleterious to the recipient thereof.

Administration of the active ingredient or pharmaceutical compositions thereof for practicing the present invention can be by any method that delivers the compounds systemically and/or locally (e.g., at the site of the bone fracture, osteotomy, or orthopedic surgery). These methods include oral routes, parenteral routes, intraduodenal routes, etc.

For topical applications, the active ingredient or a pharmaceutical composition thereof can be formulated in a suitable ointment containing the active component suspended or dissolved in one or more carriers. Carriers for topical administration of the active ingredient or a pharmaceutical composition thereof include, but are not limited to, mineral oil. liquid petrolatum, white petrolatum, propylene glycol, polyoxyethylene, polyoxypropylene compound, emulsifying wax, sugars such as lactose and water. Alternatively, the pharmaceutical compositions can be formulated in a suitable lotion or cream containing the active ingredient or a pharmaceutical composition thereof suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Depending on the particular condition, disorder or disease to be treated, additional therapeutic agents can be administered together with the active ingredient or a pharmaceutical composition thereof. Those additional agents can be administered sequentially in any order, as part of a multiple dosage regimen, from the active ingredient or a pharmaceutical composition thereof (consecutive or intermittent administration). Alternatively, those agents can be part of a single dosage form, mixed together with the active ingredient or a pharmaceutical composition thereof (simultaneous or concurrent administration).

For oral administration, a pharmaceutical composition useful in the invention can take the form of solutions, suspensions, tablets, pills, capsules, powders, granules, semisolids, sustained release formulations, elixirs, aerosols, and the like. Tablets containing various excipients such as sodium citrate, calcium carbonate and calcium phosphate are employed along with various disintegrants such as starch, preferably potato or tapioca starch, and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, t the active ingredient or a pharmaceutical composition thereof of this invention can be combined with various sweetening agents, flavoring agents, coloring agents, emulsifying agents and/or suspending agents, as well as such diluents as water, ethanol, propylene glycol. glycerin and various like combinations thereof.

The term "parenteral" as used herein refers to modes of administration which include intravenous, intramuscular, intraperitoneal, intrasternal, subcutaneous, intramedullary and intraarticular injection and infusion. A pharmaceutical composition for parenteral injection can comprise pharmaceutically acceptable sterile aqueous or nonaqueous solutions, dispersions, suspensions or emulsions as well as sterile powders for reconstitution into sterile injectable solutions or dispersions just prior to use. Aqueous solutions are especially suitable for intravenous, intramuscular, subcutaneous and intraperitoneal injection purposes. In this connection, the sterile aqueous media employed are all readily obtainable by standard techniques well-known to those skilled in the art. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The pharmaceutical compositions useful in the present invention can also contain adjuvants such as, but not limited to, preservatives, wetting agents, emulsifying agents, and dispersing agents. Prevention of the action of microorganisms can be ensured by the inclusion of various antibacterial and antifungal agents, such as for example, paraben, chlorobutanol, phenol sorbic acid, and the like. It can also be desirable to include isotonic agents such as sugars, sodium chloride, and the like. Prolonged absorption of the injectable pharmaceutical form can be brought about by the inclusion of agents that delay absorption such as aluminum monostearate and gelatin.

Administration by slow infusion is particularly useful when intrathecal or epidural routes are employed. A number of implantable or body-mountable pumps useful in delivering compound at a regulated rate are known in the art. See, e.g., U.S. Pat. No. 4,619,652.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

For purposes of transdermal (e.g., topical) administration, dilute sterile, aqueous or partially aqueous solutions (usually in about 0.1% to 5% concentration), otherwise similar to the above parenteral solutions, are prepared.

The pharmaceutical compositions useful in the invention can also be administered by nasal aerosol or inhalation. Such compositions are prepared according to techniques well-known in the art of pharmaceutical formulation and can be prepared as solutions in saline. employing benzyl alcohol or other suitable preservatives, absorption promoters to enhance bioavailability, fluorocarbons, and/or other conventional solubilizing or dispersing agents.

Compositions for rectal or vaginal administration are preferably suppositories which can be prepared by mixing the active ingredient or a pharmaceutical composition thereof with suitable non-irritating excipients or carriers such as cocoa butter, polyethylene glycol or a suppository wax which are solid at room temperature but liquid at body temperature and therefore melt in the rectum or vaginal cavity and release the drugs.

Other pharmaceutically acceptable carriers include, but are not limited to, a non-toxic solid, semisolid or liquid filler, diluent, encapsulating material or formulation auxiliary of any type, including but not limited to ion exchangers, alumina, aluminum stearate, lecithin, serum proteins, such as human serum albumin. buffer substances such as phosphates, glycine, sorbic acid, potassium sorbate, partial glyceride mixtures of saturated vegetable fatty acids, water, salts or electrolytes, such as protamine sulfate, disodium hydrogen phosphate. potassium hydrogen phosphate, sodium chloride, zinc salts, colloidal silica, magnesium trisilicate, polyvinyl pyrrolidone, cellulose-based substances, polyethylene glycol. sodium carboxymethylcellulose, polyacrylates, waxes, polyethylene-polyoxypropylene-block polymers, polyethylene glycol and wool fat.

Solid pharmaceutical excipients include, but are not limited to, starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients can be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Methods of preparing various pharmaceutical compositions with a certain amount of active ingredient are known, or will be apparent in light of this disclosure, to those skilled in this art. Other suitable pharmaceutical excipients and their formulations are described in Remington's Pharmaceutical Sciences, edited by E. W. Martin, Mack Publishing Comparry, 19th ed. 1995.

In another aspect, the invention provides a method for selection of a DAAO inhibitor, comprising selecting a drug database; removing compounds containing metal atoms and compounds with molecular weights outside the 100-700 g/mol range; selecting the compound candidates with interaction with more than three residues of Leu51, Gln53, Leu215, His217, Tyr 224, Tyr228, Ile230, Arg283 and Gly313 of DAAO and subjecting the selected compound candidates to an inhibitory activity assay.

Any drug database can be used in the method of the invention. The compounds are reduced to a subset by removing molecules containing metal atoms and molecules with molecular weights outside the 100-700 g/mol range. To assess their probable binding mode and interaction patterns in the active site of DAAO, MSD was performed on the selected compounds. From the results of MDS, nearby the DAAO residues near each compound were analyzed. According to the literature. the active site of DAAO contained the following residues: Leu51, Gln53, Leu215, His217, Tyr 224, Tyr228, Ile230, Arg283 and Gly313. The molecules with more than three residues mentioned above within 3 A distance nearby were considered candidates. The DAAO inhibitory compounds mentioned herein are obtained by performing the selection method of the invention.

EXAMPLE

Example 1 Selection of DAAO Inhibitors

Materials

D-alanine, 3-(4-hydroxyphenyl) propionic acid (HPPA), porcine kidney DAAO, peroxidase, Tris-base, esomeprazole. N-desmethylclozapine, nalbuphine, and amodiaquin were purchased from Sigma-Aldrich Co. LLC. (Sigma-Aldrich, USA). Trishydrochloride was purchased from invitrogen (Life Technologies Corporation, USA). 5-O-Desmethyl-Omeprazole and Olanzapine were purchased from Toronto Research Chemicals (Canada). PM-BRL 36583A and PM-BRL 36610A were gift from GlaxoSmithKline (United Kingdom). Duloxetine was purchased from Sequoia Research Products (United Kingdom). Black 96 well plates were purchased form Nunc (Thermo Scientific, USA).

Virtual Screening

The DAAO crystal structures was obtained from the Protein Data Bank (Schnell, E.; Sizemore, M.; Karimzadegan, S.; Chen, L.; Bredt, D. S.; Nicoll, R. A., Direct interactions between PSD-95 and stargazin control synaptic AMPA receptor number. Proc Natl Acad Sci USA 2002, 99 (21). 13902-7) (PDB id: 3G3E). Total of 1463 compounds from DrugBank (DrugBank http://www.drugbank.ca/) and our in-house collections of drug metabolites and compounds were used for the virtual screening. The compounds were reduced to a subset by removing molecules containing metal atoms and molecules with molecular weights outside the 100-700 g/mol range. The result to a total of 1367 compounds preselected for the following steps. The compounds were geometrically optimized using mmff94 (Halgren, T. A., Merck molecular force field. 1. Basis, form, scope, parameterization, and performance of MMFF94. J Comput Chem 1996, 17 (5-6), 490-519) force filed by ChemAxon (Weber, L., J Chem Base—ChemAxon. Chem World-Uk 2008, 5 (10), 65-66). DAAO crystal structure was only retained a monomer. MGL-tools package (MGL-tools package. http://mgltools.scripps.edu/) was used to remove waters and add hydrogens in the DAAO crystal structure. Compound 3-hydroxyquinolin-2(1H)-one was removed in the crystal complex while cofactor FAD was retained. Compounds partial charges were assigned using MGL-tools package (MGL-tools package. http://mgltools.scripps.edu/). Total of 1367 compounds were docked into the DAAO-FAD complex using AutoDock Vina (Trott, O.; Olson, A. J., Software News and Update AutoDock Vina: Improving the Speed and Accuracy of Docking with a New Scoring Function, Efficient Optimization, and Multithreading. J Comput Chem 2010, 31 (2), 455-461), and the docking score was based on AMBER force filed (Cornell, W. D.; Cieplak, P.; Bayly, C. I.; Gould, I. R.; Merz, K. M.; Ferguson, D. M; Spellmeyer, D. C.; Fox, T; Caldwell, J. W; Kollman, P. A., A second generation force field for the simulation of proteins, nucleic acids, and organic molecules (vol 117, pg 5179, 1995). J Am Chem Soc 1996, 118 (9), 2309-2309). The docking box was a 20 Å square which central coordination was (10.932, −36.407, 31.470) in the DAAO crystal structure. The setting of exhaustiveness value. the time spent on the search, was eight. Top 100 compounds with most favorable docking scores were selected to participate in MDS step.

Molecular Dynamic Simulation (MDS)

We chose the binding mode with the lowest energy for each compound and perform MDS process by using GROMACS version 4.5.2 and the GROMOS 53A6 force field (Oostenbrink, C.; Soares, T. A.; van der Vegt, N. F. A.; van Gunsteren, W F., Validation of the 53A6 GROMOS force field. Eur Biophys J Biophy 2005, 34 (4), 273-284). The protein structure was placed in a simple cubic periodic box of SPC216-type water molecules, and the distance between protein and each edge of the box was set as 0.9 nm. To maintain overall electrostatic neutrality and isotonic conditions, $Na^+$ and $Cl^-$ ions were randomly positioned within this solvation box. To maintain the proper structure and remove unfavorable van der Waals contacts, a 1000-step energy minimization using the steepest descent algorithm was employed with an energy minimization convergence criteria of a between-step difference smaller than 1000 kJ $mol^{-1}$ $nm^{-1}$. After the energy minimization, the system was subjected to a 1 ns molecular dynamics simulation at constant temperature (300 K), pressure (1 atm), and a time step of 0.001 ps (1 fs) with the coordinates of the systems recorded every every 1000 steps.

DAAO Enzymatic Assay

The DAAO enzymatic activity assay was modified according to the report of Oguri et al (Oguri, S., Screening of d-amino acid oxidase inhibitor by a new multi-assay method. Food chemistry 2007, 100 (2), 616). The DAAO activity was measured by using substrate D-alanine reaction produced hydrogen peroxide ($H_2O_2$) to further react with 3-(4-hydroxyphenyl) propionic acid (HPPA). The HPPA were oxidized by $H_2O_2$ and peroxidase to become the fluorogenic dimer which was measured to represent the activity of DAAO. The substrate of DAAO was prepared in 50 mM D-alanine (dissolved in 0.2 M Tris-HCl buffer, pH 8.3). A 100 ul of D-alanine solution was mixed with 4 ul (in 100%) dimethyl sulfoxide, DMSO) of different concentrations of drugs ranging from 31.36 nM, 94.08 nM, 0.28 uM, 0.85 uM, 2.54 uM, 7.62 uM, 22.86 uM, 68.59 uM, 0.21 mM, 0.62 mM, 1.85 mM, 5.56 mM, 16.67 mM, and 50.00 mM with a final DMSO concentrations of 0.167% in each reaction concentration. A 10 ul of D-alanine and drug mixture was incubated with 220 ul of Reaction Master Mix in black 96 well plate at 37° C. for 5 min. The Reaction Master Mix contained 110 ul of 5 U/mL porcine kidney DAAO (Sigma-Aldrich, USA) solution (dissolved with 0.2 M Tris-HCl buffer, pH 8.3), 1.1 mL of 15 U/mL peroxidase solution (dissolved with 0.2 M Tris-HCl buffer, pH 8.3), 1.1 mL of 20 mM HPPA solution (dissolved with 0.2 M Tris-HCl buffer, pH 8.3), and 2.2 ml of 2 M Tris-HCl buffer (pH 8.3) for 110 reaction assays.

Fluorescence intensity (Fs) was measured at 405 nm by irradiation excitation at 320 nm. The higher is the DAAO enzymatic activity, the higher is the fluorescence intensity. The fluorometric inhibition indicator (Fi) was obtained from the following equation: $Fi=(Fs-F_{Drug})/(F_{DMSO})$. Where the fluorescent drug blank ($F_{Drug}$) were measured in the drug mixture solution (using 0.2 M Tris HCl buffer, pH 8.3, without D-alanine). A DMSO blank ($F_{DMSO}$) was measured under a 100% DMSO solution. Although, in the assay for D-amino acid oxidase, FAD was generally included in the reaction mixture because this co-factor is easily dissociated from the holoenzyme, the present method was performed without FAD. The inhibitory effect of DAAO inhibitors was compared by using inhibitory concentrations which reduce 50% of DAAO activity ($IC_{50}$). The $IC_{50}$ value was calculated by GraphPad Prism, version 5 software (GraphPad Software, Inc., La Jolla, Calif.) (GraphPad Prism 5, GraphPad software Inc: California, USA) through nonlinear regression model.

Results

Selection of Candidate Compounds.

To assess their probable binding mode and interaction patterns in the active site of DAAO, MSD was performed on the 100 selected compounds. The GROMOS 53A6 force is field (Oostenbrink, C.; Soares, T A.; van der Vegt, N. F. A.; van Gunsteren, W. F., Validation of the 53A6 GROMOS force field. Eur Biophys J Biophy 2005, 34 (4), 273-284) and the SPC216-type water molecules were used to simulate the complex system. $Na^+$ or $Cl^-$ would be added if the systems were not the electrostatic neutrality conditions. From the results of MDS, nearby the DAAO residues near each compound were analyzed. According to the literature, the active site of DAAO contained the following residues: Leu51, Gln53, Leu215, His217, Tyr 224, Tyr228, Ile230, Arg283 and Gly313. (Sparey, T et al., Bioorg Med Chem Lett 2008, 18 (11), 3386-91; Kawazoe, T. et al, Biochem Bioph Res Co 2007, 355 (2), 385-391; Duplantier, A. J. et al.. J Med Chem 2009, 52 (11), 3576-3585). The molecules with more than three residues mentioned above within 3 Å distance nearby were considered candidates. Nine candidates could be acquired from commercial sources for testing and proceed with in vitro study. Name and structure of the compounds with their $IC_{50}$ are listed in Table 1.

Experimental Evaluation.

Figure 2:
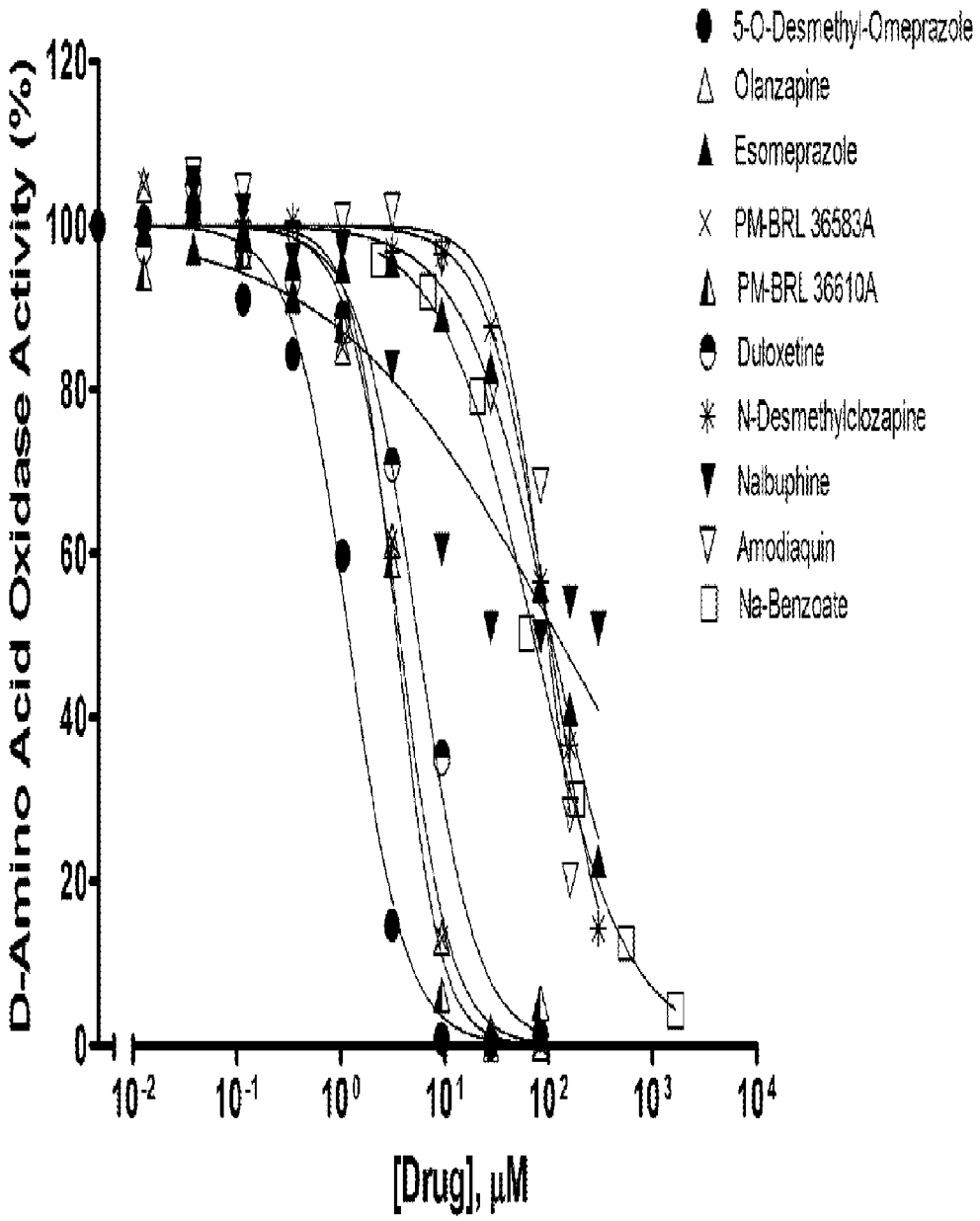
FIG. 2 shows the $IC_{50}$ of the selected drugs.

The compounds were tested in fluorescence intensity (Fs) measured at 405 nm by irradiation excitation at 320 nm. The DAAO enzymatic activities after the incubation with different concentrations of sodium benzoate showed that the $IC_{50}$ (causing 50% of DAAO activity reduction of sodium benzoate concentration) is around 71.74 uM (95% confidence interval ranging from 62.67 uM to 82.13 uM). For other known drugs, we also performed the enzymatic assay to validate the $IC_{50}$. The $IC_{50}$ of each known drug were showed in Table 1 and the IC50 were plotted in FIG. 2. The higher the DAAO enzymatic activity is, the higher the fluorescence intensity is. All of the nine compounds had IC50 values located micromolar range. There were five compounds were confirmed to have inhibitory activity with the $IC_{50}$ values ranging from 1 to 10 uM. The five drug repurposing candidates were 5-O-Desmethyl-Omeprazole, Olanzapine, PM-BRL 36583A, PM-BRL 36610A and Duloxetine. Among them, 5-O-Desmethyl-Omeprazole had the best inhibition with an $IC_{50}$ value of 1.19 uM in the enzymatic assay test. 5O-Desmethyl-Omeprazole is the metabolite of Omeprazole which is known for its therapeutic use in the treatment of dyspepsia, peptic ulcer disease and gastroesophageal reflux disease.

TABLE 1

Ranking of the compounds by their DAAO $IC_{50}$

| Rank | Compound Name | Structure | $IC_{50}$ (uM) |
|---|---|---|---|
| 1 | 5-O-Desmethyl-Omeprazole (RS-D7) | 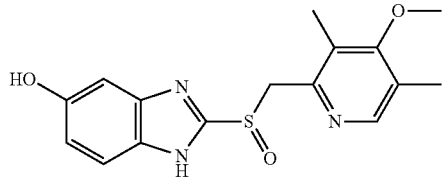 | 1.185 |

TABLE 1-continued
| Ranking of the compounds by their DAAO $IC_{50}$ | | | |
|---|---|---|---|
| Rank | Compound Name | Structure | $IC_{50}$ (uM) |
| 2 | Olanzapine | 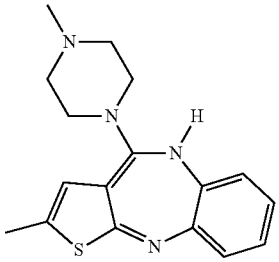 | 3.278 |
| 3 | PM-BRL 36610A | 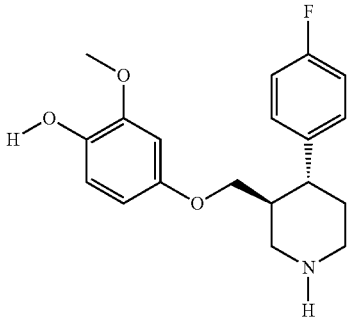 | 3.45 |
| 4 | PM-BRL 36583A | 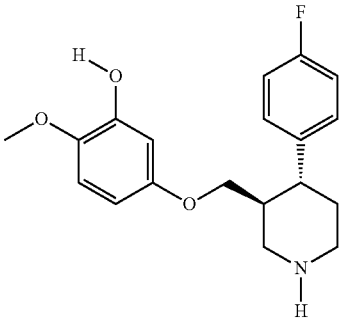 | 3.669 |
| 5 | Duloxetine | 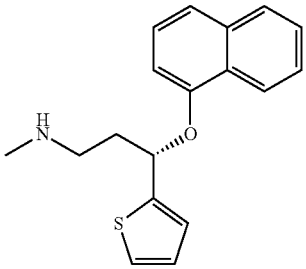 | 5.469 |
| 6 | Amodiaquin | 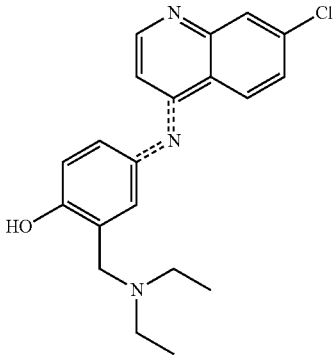 | 97.62 |

TABLE 1-continued

| Ranking of the compounds by their DAAO $IC_{50}$ | | | |
|---|---|---|---|
| Rank | Compound Name | Structure | $IC_{50}$ (uM) |
| 7 | N-Desmethylclozapine | | 102.4 |
| 8 | Esomeprazole | | 106 |
| 9 | Nalbuphine | | 120.9 |

Docking and Interaction Studies of 5-O-Desmethyl-Omeprazole at DAAO-FAD Structure.

The previous studies indicated that several inhibitors with available DAAO-FAD-compound crystal complex from PDB (Schnell, E.; et al., Proc Natl Acad Sci USA 2002, 99 (21), 13902-7), for example, imino-DOPA (Kawazoe, T. et al., Biochem Bioph Res Co 2007, 355 (2), 385-391), 3-hydroxyquinolin-2(1H)-one (Duplantier. A. J. et al., J Med Chem 2009, 52 (11), 3576-3585) and 4H-Furo[3,2-b]pyrrole-5-carboxylic acid (Sparey, T. et al.; Bioorg Med Chem Lett 2008, 18 (11), 3386-91). Their PDB ids were 2E82, 3G3E and 3CUK, respectively. From the structural analysis, the three compounds were located near FAD. Key interactions might arise from the residues Leu51, Gln53, Leu215, His217, Tyr 224, Tyr228, Ile230, Arg283 and Gly313. Also most of the key residues would form the hydrogen bonds with the compounds except Leu51, Leu215 and Ile230. (Sparey, T. et al., Biochem Bioph Res Co 2007, 355 (2), 385-391; Duplantier, A. J. et al., J Med Chem 2009, 52 (11), 3576-3585)

We analyzed the docking and MDS results of the DAAO-FAD-5-O-Desmethyl-Omeprazole complex as shown in FIG. 1. The relative binding poses and positions of 5-O-Desmethyl-Omeprazole and 3-hydroxyquinolin-2(1H)-one (Duplantier, A. J. et al., J Med Chem 2009, 52 (11), 3576-3585) (which obtained from PDB crystal structure) was displayed in FIG. 1(a). The 3-hydroxyquinolin-2(1H)-one was close to FAD in FIG. 1(a). However, while the benzimidazole part of the 5-O-Desmethyl-Omeprazole was located near FAD, the binding pose was different from the compounds described above. The pyridine ring of the 5-O-Desmethyl-Omeprazole, locates in other region far from the FAD. In FIGS. 1(b) and (d), the residues interacted with the 5-O-Desmethyl-Omeprazole and included in Leu51, Pro54, Leu56, Trp107, His217, Asp218, Tyr224 and Gly313. Among them, Leu56, Trp107 and Tyr224 formed the hydrogen bonds with 5-O-Desmethyl-Omeprazole. From these analysis, we suggested that the 5-O-Desmethyl-Omeprazole had a dissimilar binding mode from the 3-hydroxyquinolin-2(1H)-one, and the hydrogen bonds also played an important role in the complex system.

Example 2 Pre-Clinical Drug Testing in Mice

In complementary to human studies, a powerful approach is the use of animal models to identify functional consequence and to screen out potential compounds in populations with less or no genetic heterogeneity. In the pre-clinical drug testing, animal model provides an important tool in pharmaceutical discovery and development efforts (Everitt J. I, Toxicologic Pathology. 2015, 43(1), 70-7). Indeed, animal models not only play an indispensable role in the discovery and verification of potential drugs/treatments but also provide a feasible approach to elucidate causal relationships between genes and related symptoms (Lai, W. S et al., Current Pharmaceutical Design, 2014, 20(32), 5139-50). One of hand, the healthy animal model can help to ensure the quality, potency, and safety of the therapeutic potential (Lebron, J. A et al., Expert Review of Vaccines, 2005, 4(6), 855-66). On the other hand, the generation of genetically modified mice or transgenic mice with specific genes allows researchers to study the biological functions of schizophrenia susceptibility genes in vivo. In the dopamine hypothesis, for example, it was reported that amphetamine/methamphetamine, which increases synaptic dopamine levels, caused psychosis in normal individual or exacerbates psychosis in individuals with schizophrenia (Lieberman, J. A et al., Psychopharmacology (Berl), 1987, 91(4), 415-433; Grant, K. M et al., Journal of Neuroimmune Pharmacology, 2012, 7(1), 113-139). Accordingly, amphetamine/methamphetamine administrations in mice provide a good model to further investigate the pathophysiology of schizophrenia. However, focusing on the dopamine system has led to limited progress in understanding the mechanism of the cognitive dysfunction and negative symptoms of schizophrenia (Miyamoto, S et al., Molecular Psychiatry, 2012, 17, 1206-1227). Therefore, to improve understanding of the pathology and symptomatology (particularly cognitive and negative symptoms) of schizophrenia, the dysfunction of glutamate pathway is one of the prominent mechanisms behind the disease's pathophysiology (Egerton, A et al., Current Pharmaceutical Biotechnology, 2012, 13(8), 1500-1512; Moghaddam, B; Javitt, D, Neuropsychopharmacology, 2012, 37(1), 4-15).

Along the same line, accumulating studies have shown that NMDA receptor antagonists, such as phencyclidine (PCP) and dizocilpine (MK-801), produce "schizophrenia-like" symptoms in healthy individuals (Javitt, D. C; Zukin, S. R, The American Journal of Psychiatry, 1991, 148, 1301-1308; Krystal, J. H et al., Archives of General Psychiatry, 1994, 51, 199-214), and dysregulated NMDA receptor subunits are seen in postmortem tissue from schizophrenia patients and animal models of NMDA antagonism (Gunduz-Bruce, H et al., Brain Research Reviews, 2009, 60, 279-286; Lisman, J. E et al., Trends in Neurosciences, 2008, 31, 234-242). According to the legal restriction to limit the PCP use, MK-801 is a better NMDA antagonist to bind inside the ion channel of NMDA receptor thus preventing the flow of ions. Besides, emerging evidence also exhibits the ability of MK-801 to induce cognitive deficits and negative symptoms of relevance to schizophrenia in mice (Neill, J. C; Barnes et al., Pharmacology & Therapeutics, 2010, 128(3), 419-32; Bubeniková-Valesová, V et al., Neuroscience & Biobehavioral Reviews, 2008. 32(5), 1014-23). It is worth taking advantage of MK-801 mouse model of schizophrenia to show phenomenological validity and is suitable for searching for new substances with antipsychotic effects.

The Results of RS-D7 In Vivo Efficacy in Mice

Taking advantage of wild-type (WT, healthy) mouse and pharmacologic animal models of schizophrenia, such as MK-801 and methamphetamine mouse model of schizophrenia, as the well-established animal models of schizophrenia, we investigate the therapeutic potential of RS-D7, a DAO inhibitor, on the alleviation of schizophrenia-related negative and cognitive deficits. A serial of behavioral tasks has been selected and conducted for mimicking the cognitive (e.g., prepulse inhibition) and negative symptoms (e.g., sucrose preference test and hot plate test) of schizophrenia in healthy control mice or pharmacological mouse model of schizophrenia (Lai, W. S et al., Current Pharmaceutical Design, 2014, 20(32), 5139-50). The pharmacological animal model of schizophrenia is due in part to similarities in clinical presentation and response to treatment. These behavioral tasks have been evaluated with varying degrees of test validities for assessing schizophrenia-relevant behavioral deficits in mice. Different batches of male adult C57/B16 mice were used and the details of different behavioral tasks were described elsewhere.

Figure 3:
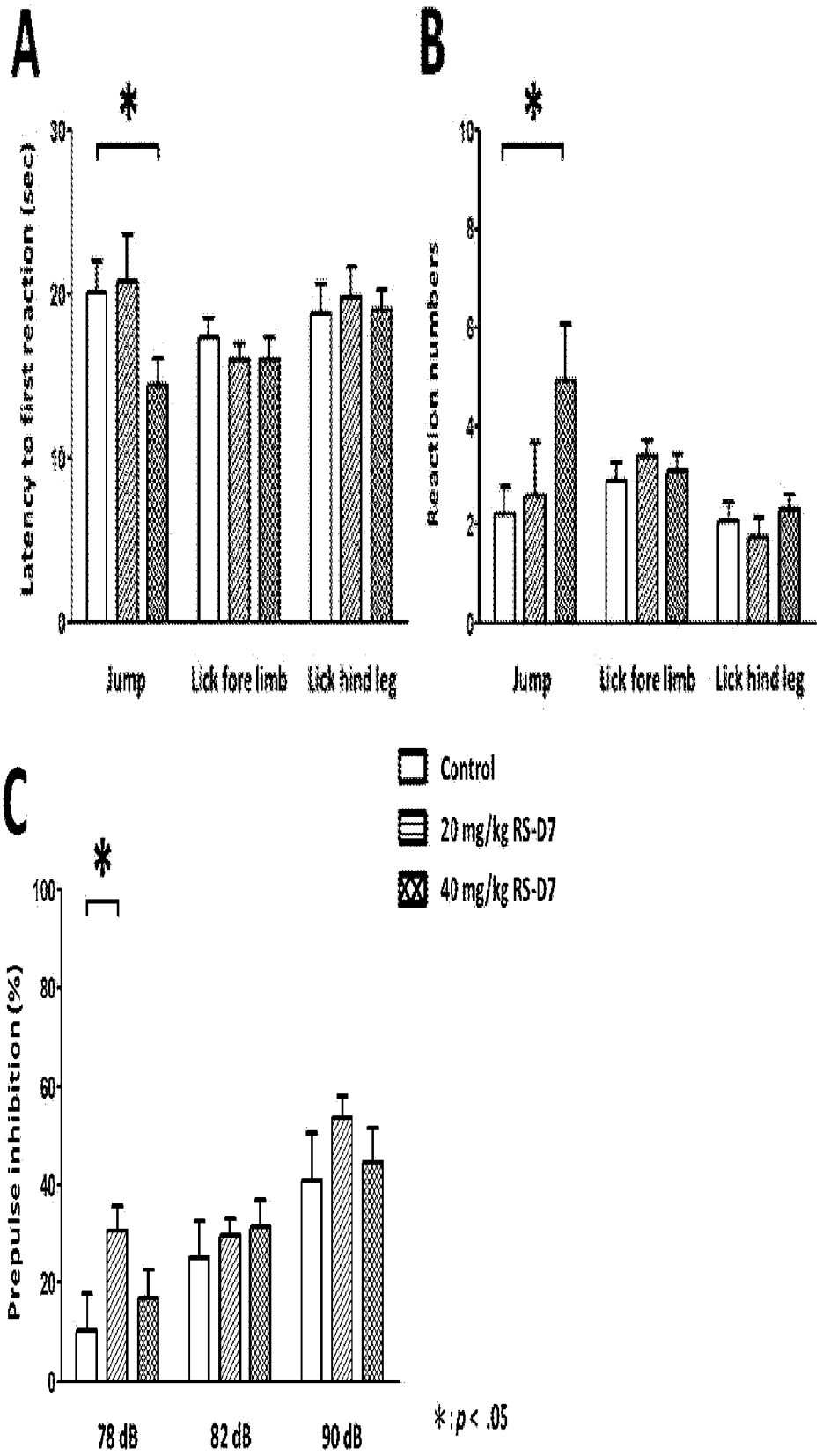
FIG. 3 shows that the injection of RS-D7 increases nociception function (A & B) and sensorimotor gating function (C) in mice.

In WT Mouse Model:

For schizophrenia-like negative symptoms in mice, hot plate test was used to assess basic pain and nociception function in mice. Compared with the WT controls, the latency of mouse first reaction (i.e., jump) was accelerated and the numbers of jump was increased on the 55° C. hot plate test after 40 mg/kg RS-D7 (i.p.) injection (FIGS. 3A and 3B). These results suggest that the injection of 40 mg/kg RS-D7 increase nociception function in mice.

To assess schizophrenia-like cognitive function in mice, prepulse inhibition (PPI) was used to evaluate sensorimotor gating functions in mice after RS-D7 injection. Prepulse Inhibition (PPI) is a neurological phenomenon in which a weaker prestimulus (prepulse) inhibits the reaction of an organism to a subsequent strong startling stimulus (pulse). The deficits of PPI are noted in some disorders, including patients with schizophrenia. Compared with saline controls, the injection of 20 mg/kg RS-D7 (i.p.) induced a greater PPI under 78 dB prepulse (FIG. 3C). This finding suggests that 20 mg/kg RS-D7 increased the sensorimotor gating function in mice.

In Methamphetamine Mouse Model of Schizophrenia

Figure 4:
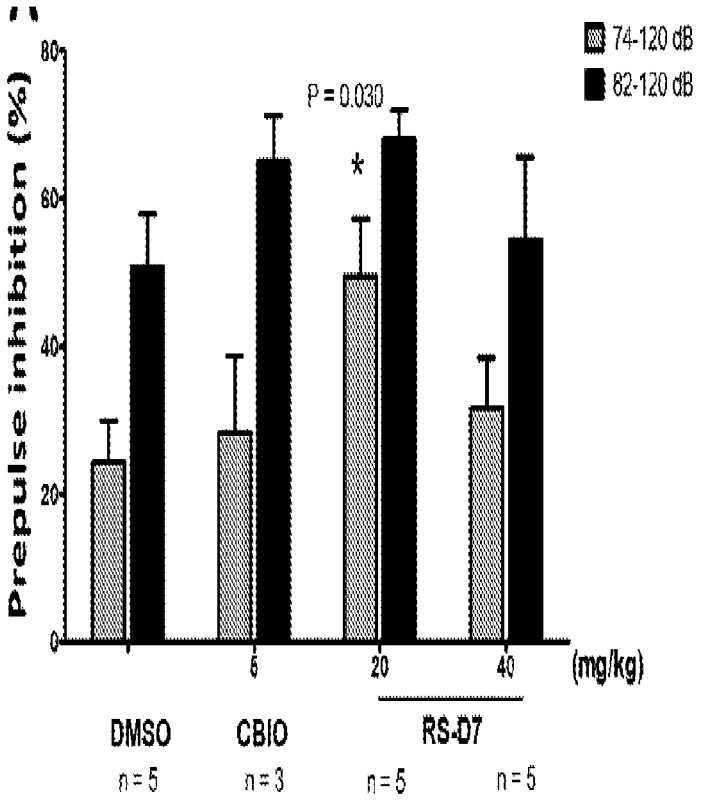
FIG. 4 shows that the injection of RS-D7 alleviates sensorimotor gating deficit in ICR mice injected with methamphetamine (3 mg/kg).

Methamphetamine is a potent psychostimulant that increases the amount of extracellular dopamine in the brain. Methamphetamine (or amphetamine)-induced psychosis model has been well-established and useful for schizophrenia in laboratory animals. Compared with the DMSO and CBIO controls, the injection of 20 mg/kg RS-D7 (i.p.) induce a greater PPI in ICR mice with methamphetamine injection (3 mg/kg, i.p.), especially in 74 dB prepulse (FIG. 4). This finding suggests that the injection of 20 mg/kg RS-D7 increased sensorimotor gating function in methamphetamine-treated mice.

Figure 5:
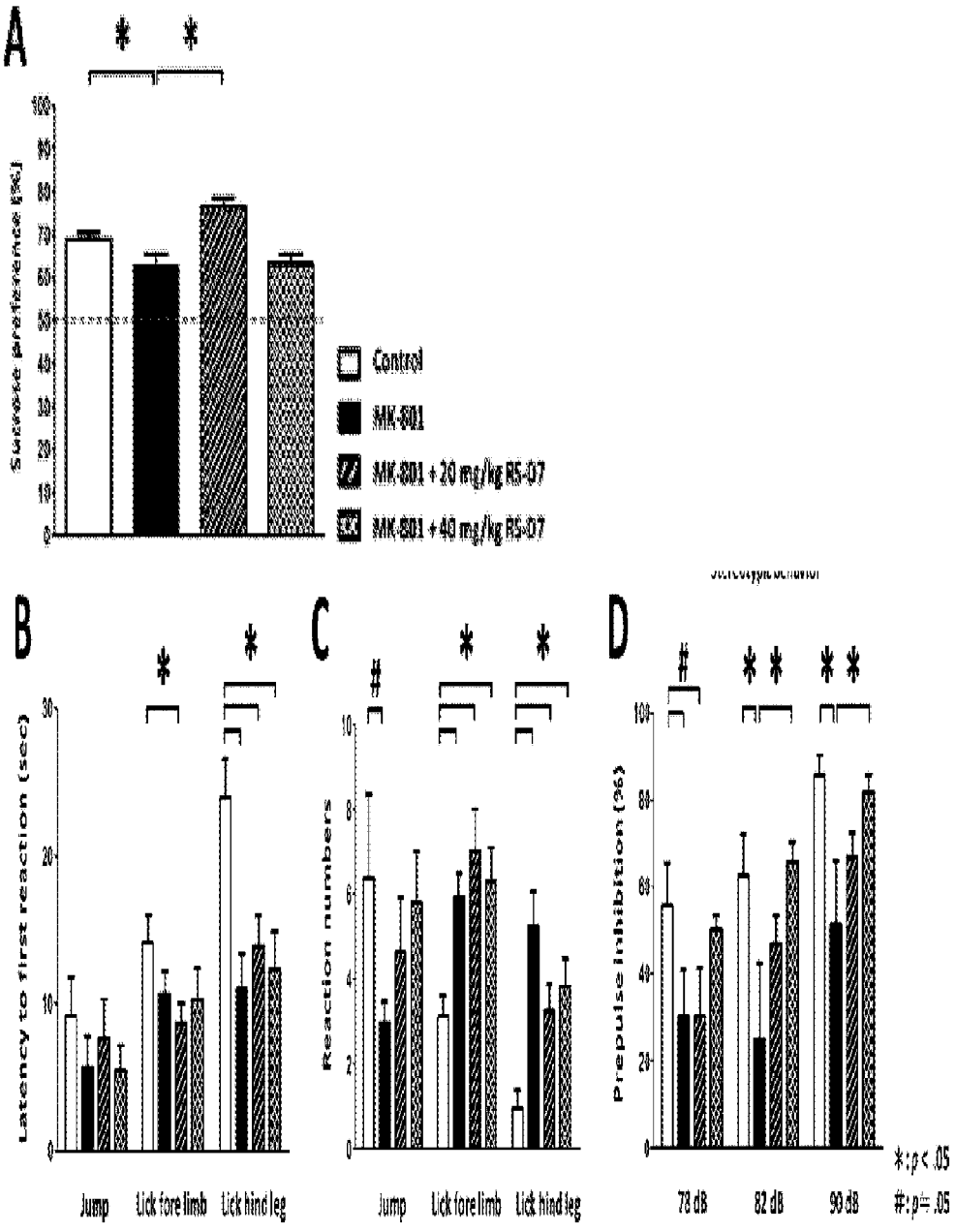
FIG. 5 shows that the injection of RS-D7 alleviates MK-801 (0.2 mg/kg) induced behavioral deficits in (A) sucrose preference test, (B & C) hot plate test, and (D) prepulse inhibition in mice.

In MK-801 Mouse Model of Schizophrenia:

MK-801 is a non-competitive NMDA receptor antagonist. An injection and chronic injections of MK-801 provide a potential animal model to mimic both the negative and cognitive symptoms of schizophrenia. C57/B16 Mice received an acute administration of MK-801 (0.2 mg/kg, i.p.) and the doses of MK-801 were chosen to avoid stereotypic behaviors in the open field. Compared with the saline controls, a significant reduction of sucrose uptake was observed after acute MK-801 injection. Intriguingly, the injection of 20 mg/kg RS-D7 rescued the MK-801 induced deficit in mice (FIG. 5A). This result suggests that acute RS-D7 injection alleviated MK-801-induced anhedonia in the sucrose preference test.

For hot plate test, the injection of RS-D7 also alleviated the MK-801-induced alteration of latency and reaction numbers in the hot plate test, respectively (FIGS. 5B and 5C). For PPI, as depicted in FIG. 5D, mice with acute MK-801 injection exhibited a profound reduction of acoustic PPI. Importantly, the injection of 40 mg/kg RS-D7 significantly alleviated MK-801 induced PPI deficit in these mice. These results suggest that RS-D7 can normalize MK-801-induced dysfunction in mice.

Collectively, all findings from our healthy control mice and pharmacological mouse models of schizophrenia support that RS-D7 has potential to improve or alleviate schizophrenia-related negative and cognitive symptoms in mice.

What is claimed is:

1. A method of treating a disease in a subject in need thereof, comprising administering to the subject an effective amount of 5-O-desmethyl-omeprazole or a therapeutically acceptable salt, solvate, *prodrug,* or stereoisomer thereof, or a pharmaceutical composition containing 5-O-desmethyl-omeprazole, wherein the disease is selected from the group consisting of schizophrenia, schizoaffective disorder, mild cognitive impairment (*MCI*), Tourette Syndrome, ataxia, *post-traumatic stress disorder* (PTSD), dementia, loss of memory and/or cognition associated with neurodegenerative diseases, and loss of neuronal function characteristic of neurodegenerative diseases.

2. The method of claim 1, wherein the effective amount of 5-O-desmethyl-omeprazole is 2 mg/kg body weight to 5 g/kg body weight.

3. The method of claim 1, wherein the disease is treated via *D-amino acid oxidase* (DAAO) inhibition.

4. The method of claim 1, wherein the schizophrenia and schizoaffective disorder include negative, cognitive, positive, and general psychopathology symptom domains.

5. The method of claim 1, wherein the disease is [mild cognitive impairment] *MCI* or schizophrenia.

6. The method of claim 1, wherein the disease is ataxia.

7. The method of claim 1, wherein the disease is schizoaffective disorder.

8. The method of claim 1, wherein the disease is Tourette Syndrome.

9. The method of claim 1, wherein the disease is PTSD.

10. The method of claim 1, wherein the disease is dementia, loss of memory and/or cognition associated with neurodegenerative diseases, or loss of neuronal function characteristic of neurodegenerative diseases.

11. The method of claim 1, wherein the subject is a human.

12. The method of claim 1, wherein the pharmaceutical composition comprises a pharmaceutical acceptable carrier and/or an excipient.

13. The method of claim 1, wherein the 5-O-desmethyl-omeprazole or [a] *the* therapeutically acceptable salt, solvate, *prodrug,* or stereoisomer thereof or the pharmaceutical composition is administered to the subject [orally] *by oral*, [parenterally] *parenteral*, [intravenously] *intravenous*, [intramuscularly] *intramuscular*, [intraperitoneally] *intraperitoneal*, [intrasternally] *intrasternal*, [subcutaneously] *subcutaneous*, intramedullary, [intraarticularly] *intraarticular, infusion, intrathecal, epidural*, [intraduodenally] *intraduodenal*, [or transdermally] *transdermal, nasal aerosol, inhalation, rectal, or vaginal administration*.

* * * * *